United States Patent
Benoit et al.

(10) Patent No.: US 10,111,739 B2
(45) Date of Patent: Oct. 30, 2018

(54) METHOD FOR REHYDRATION OF LYOPHILIZED BIOLOGIC MATERIALS

(71) Applicant: C.R. Bard, Inc., Murray Hill, NJ (US)

(72) Inventors: Bethanie J. Benoit, North Smithfield, RI (US); Karen Elizabeth Kullas, Berkely, MA (US); Devang Vijay Shah, Wrentham, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 454 days.

(21) Appl. No.: 14/861,281

(22) Filed: Sep. 22, 2015

(65) Prior Publication Data

US 2016/0008120 A1    Jan. 14, 2016

Related U.S. Application Data

(62) Division of application No. 13/424,794, filed on Mar. 20, 2012, now Pat. No. 9,155,606.

(51) Int. Cl.
*A61F 2/00* (2006.01)
*B65D 77/04* (2006.01)
(Continued)

(52) U.S. Cl.
CPC .......... *A61F 2/0095* (2013.01); *A61F 2/0063* (2013.01); *A61J 1/10* (2013.01);
(Continued)

(58) Field of Classification Search
CPC ............... A61F 2/0095; A61L 27/3683; A61L 27/3691; B65B 55/22; B65B 2220/16; B65D 77/04; B65D 81/22
(Continued)

(56) References Cited

U.S. PATENT DOCUMENTS

| 2,902,146 A | 9/1959 | Doherty |
| 3,043,067 A * | 7/1962 | Rynkiewicz et al. ........................ A61B 17/06133 53/431 |

(Continued)

FOREIGN PATENT DOCUMENTS

WO         02/16209 A1    2/2002

OTHER PUBLICATIONS

European Examination Report dated Jul. 28, 2016 for Application No. 13 159 810.4, 5 pages.

*Primary Examiner* — Stephen F Gerrity
(74) *Attorney, Agent, or Firm* — Wolf, Greenfield & Sacks, P.C.

(57) ABSTRACT

The present invention is a method and an apparatus for packaging lyophilized implants and other medical devices. In accordance with the invention, a lyophilized implant may be packaged for delivery to the surgical site in a sealed, flexible/expandable, sterile inner pouch. The inner pouch may be further packaged within an outer, sterile package. The inner pouch contains a resealable port through which rehydration liquid may be introduced into the inner pouch without opening the inner pouch. The inner pouch may be made of a flexible, substantially non-stretchable material so that the pouch can expand only to a predetermined maximum size to accept a predetermined volume of rehydration liquid. After rehydration, any excess rehydration liquid within the pouch may be removed via the same port. Next, the pouch is opened via a second opening to expose the implant for removal from the package.

8 Claims, 5 Drawing Sheets

(51) Int. Cl.
   *B65D 75/58* (2006.01)
   *B65D 30/24* (2006.01)
   *B65D 81/22* (2006.01)
   *B65B 55/22* (2006.01)
   *A61J 1/10* (2006.01)
   *A61J 1/20* (2006.01)

(52) U.S. Cl.
   CPC ............ *A61J 1/2096* (2013.01); *B65B 55/22* (2013.01); *B65D 31/147* (2013.01); *B65D 75/5855* (2013.01); *B65D 77/04* (2013.01); *B65D 81/22* (2013.01)

(58) Field of Classification Search
   USPC .................. 53/425, 426, 431; 206/205, 438; 623/920
   See application file for complete search history.

(56) References Cited

U.S. PATENT DOCUMENTS

| | | | |
|---|---|---|---|
| 3,315,802 A | 4/1967 | Lonholdi et al. | |
| 3,326,450 A | 6/1967 | Langdon | |
| 3,342,326 A | 9/1967 | Zackheim | |
| 4,176,746 A | 12/1979 | Kooi | |
| 4,197,947 A * | 4/1980 | Zaidi | B65D 77/2024 206/438 |
| 4,467,588 A | 8/1984 | Carveth | |
| 4,511,533 A | 4/1985 | Guadagno et al. | |
| 4,537,305 A | 8/1985 | Takanashi | |
| 4,557,381 A | 12/1985 | Whitney | |
| 4,597,765 A | 7/1986 | Klatt | |
| 4,941,308 A * | 7/1990 | Grabenkort et al. | A61M 25/002 53/431 |
| 5,031,762 A | 7/1991 | Heacox | |
| 5,217,118 A | 6/1993 | Mochizuki et al. | |
| 5,236,088 A * | 8/1993 | Dhority et al. | A61F 2/0095 206/205 |
| 5,392,918 A | 2/1995 | Harrison | |
| 5,480,424 A * | 1/1996 | Cox | A61F 2/0095 623/2.15 |
| 5,549,338 A | 8/1996 | Wilkes | |
| 5,947,274 A | 9/1999 | Taskis et al. | |
| 6,050,400 A | 4/2000 | Taskis et al. | |
| 6,149,655 A | 11/2000 | Constantz et al. | |
| 6,622,864 B1 | 9/2003 | Debbs et al. | |
| 6,648,133 B1 | 11/2003 | Blaschke et al. | |
| 6,739,112 B1 * | 5/2004 | Marino | B65B 55/22 53/431 |
| 6,935,889 B2 | 8/2005 | Picardo et al. | |
| 7,040,485 B2 | 5/2006 | Gupta et al. | |
| 7,229,820 B2 | 6/2007 | Wilson | |
| 7,506,759 B2 | 3/2009 | Iwatschenko | |
| 7,594,577 B2 | 9/2009 | Iwatschenko | |
| 7,670,384 B2 | 3/2010 | Kumar et al. | |
| 2003/0108239 A1 | 6/2003 | Su et al. | |
| 2006/0108239 A1* | 5/2006 | Iwatschenko | A61B 17/8847 206/63.5 |
| 2006/0280803 A1 | 12/2006 | Kumar et al. | |
| 2007/0074989 A1 | 4/2007 | Merboth et al. | |
| 2007/0074990 A1 | 4/2007 | Merboth et al. | |
| 2007/0077280 A1 | 4/2007 | Collinge et al. | |
| 2007/0092398 A1 | 4/2007 | McDonald | |
| 2007/0098755 A1* | 5/2007 | Patel et al. | A61F 2/0059 424/423 |
| 2007/0154515 A1* | 7/2007 | Johnson et al. | A61F 2/0095 424/423 |
| 2007/0224587 A1* | 9/2007 | Forsell et al. | A01N 1/02 435/1.1 |
| 2008/0125721 A1 | 5/2008 | Timm | |
| 2008/0128296 A1 | 6/2008 | Stopek et al. | |
| 2009/0137042 A1 | 5/2009 | Govil | |
| 2009/0209031 A1 | 8/2009 | Stopek | |
| 2013/0233736 A1* | 9/2013 | Hess et al. | B65D 81/22 53/431 |
| 2013/0248386 A1 | 9/2013 | Benoit et al. | |

* cited by examiner

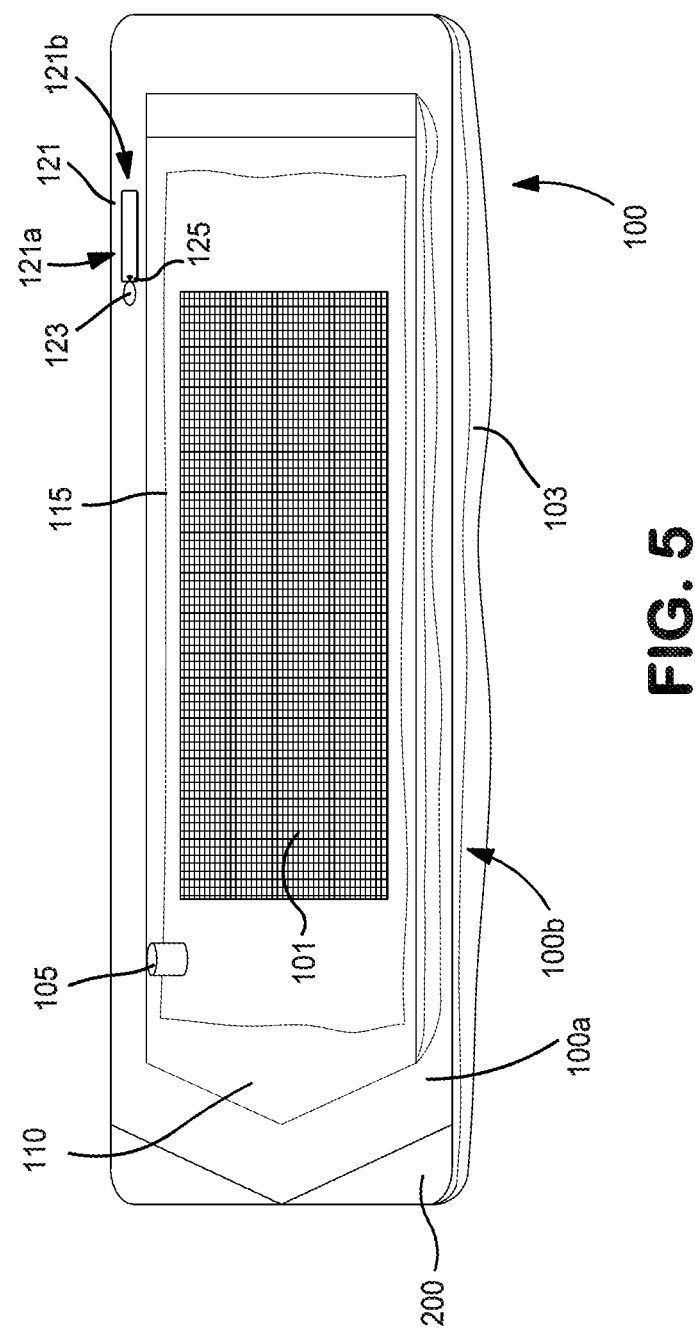

METHOD FOR REHYDRATION OF LYOPHILIZED BIOLOGIC MATERIALS

CROSS-REFERENCE TO RELATED APPLICATIONS

This application is a divisional of U.S. application Ser. No. 13/424,794, filed Mar. 20, 2012, the entire disclosure of which is hereby incorporated herein by reference.

FIELD OF INVENTION

The invention relates to packaging and rehydration of biologic materials and/or medical devices.

BACKGROUND OF THE INVENTION

It is well known to repair soft tissue defects, such as hernia ruptures and the like, with implants that temporarily or permanently replace the damaged or missing tissue. Such implants may comprise sheets of woven polymeric materials or animal tissue, such as acellular human or porcine dermis. Examples of such products currently on the market include AlloMax™, which is an acellular human dermis surgical graft product, and Collamend™ FM, which is a fenestrated acellular porcine dermal collagen implant product, both products available from Davol, Inc., a subsidiary of C. R. Bard, Inc. of Warwick, R.I., USA.

Such implants often are packaged in a lyophilized condition (i.e., dehydrated) and must be rehydrated in the sterile surgical theater just prior to implantation. The implants also may be impregnated with antibiotics or other drugs that the implant will elute into the surrounding tissue after implantation.

The conventional processes for rehydrating such lyophilized implants leave much to be desired. In one technique, the implant is removed from its sterile packaging within the sterile surgical theater and placed in a sterile basin. A basin of appropriate size that fits the implant but does not require excessive amounts of saline (or other rehydration liquid) may not be available.

Then, a sufficient amount of the rehydration liquid is poured into the basin to submerge the implant therein. Many, if not most, implants float in saline. Hence, it frequently is necessary to place a sterile surgical instrument on top of the implant within the basin in order to keep it submerged in the rehydration liquid.

Furthermore, the amount of rehydration liquid placed in the basin is not well controlled and, in fact, if the basin is much larger than the implant, it may require an excessive amount of rehydration liquid just to submerge the implant. Particularly, often, an implant can become overhydrated by exposure to too much liquid or for too long a period of time. This is a particular issue, for instance, for antibiotic or drug eluting implants. Specifically, too much of the antibiotic may leach out of the implant while it is being rehydrated if it is placed in an excessive amount of rehydration liquid or left in the rehydration liquid for an excessive amount of time.

On the other hand, it also is possible to put too little rehydration liquid into the basin, resulting in under-hydration of the implant or an extended rehydration period.

Yet further, the rehydration process can be messy because the basin has a wide opening and it is easy to knock the basin about in the operating room, causing spillage, mess, and slippery floors, all of which could lead to problems during the surgery. In addition, spillage of liquid, particularly if it contains an antibiotic, may contaminate other sterile items on the operative field.

Further, the wide opening of the basin allows for evaporation of the rehydration liquid to occur freely. Evaporation is not typically a problem if the rehydration liquid if saline. However, it is not uncommon for the rehydration liquid to contain additives that may be highly volatile and may evaporate very quickly once exposed to the room air. Finally, if the basin is open on top, there is a potential that air-borne contaminants may settle on the implant.

Another common technique for rehydrating lyophilized implants is to package the implant along with a rehydration tray. The process is substantially similar to that described above in connection with the use of sterile basins, but using the tray supplied with the implant as a substitute for the basin. The implant is removed from its sterile packaging and placed in the tray supplied with the implant and the rehydration liquid is poured over it. The use of rehydration trays specifically provided with the implant typically eliminates the problem of the rehydration vessel being ill-sized for the particular implant. However, it still suffers from the same issues of spillage, evaporation, flotation of the implant, the potential for air-borne contaminants to settle on the implant, and poor control of the amount of rehydration liquid so that the implant may be either under-hydrated or over-hydrated. Even further, the trays are single-use disposable trays and thus are often very flimsy and, therefore, prone to spillage, dropping, dropping of the implant from the tray, breakage, and failure.

SUMMARY OF THE INVENTION

The present invention is a method and an apparatus for packaging lyophilized implants, biologic materials, and other medical implements that minimizes the possibility of under- or over-hydration of the implant, prevents spillage of the rehydration liquid or implant, avoids the use of ill-sized rehydration vessels, and eliminates evaporation of the rehydration liquid. In accordance with one aspect of the invention, a lyophilized implant may be packaged for delivery to the surgical site in a sealed, flexible/expandable, sterile inner pouch. The inner pouch may be further packaged within an outer sterile package. The inner package contains a port, preferably a self-sealing needleless port through which rehydration fluid and/or other materials, such as medications or growth factors, may be introduced into the inner pouch via a needleless syringe without substantially opening the inner pouch. The pouch may be made of a foil or other flexible, but substantially non-stretchable, material so that the inner pouch can expand to accept only a predetermined amount of rehydration liquid, sufficient to reconstitute the lyophilized biologic implant material therein.

After rehydration for the desired amount of time, any remaining excess rehydration liquid within the pouch may be removed via the same port. The preferred embodiment would permit only the optimal volume of rehydration liquid to be added to the inner pouch.

Next, the inner pouch is opened via a different opening mechanism from the aforementioned rehydration port to expose the implant for removal from the package and implantation into the patient. The different opening may comprise a cover or other portion that is peelable or otherwise separable from the remainder of the pouch so as to provide a large enough opening to remove the implant from the pouch therethrough.

BRIEF DESCRIPTION OF THE DRAWINGS

FIG. 5 is a perspective view of a second embodiment of the invention.

DESCRIPTION OF THE PREFERRED EMBODIMENTS

Figure 1:
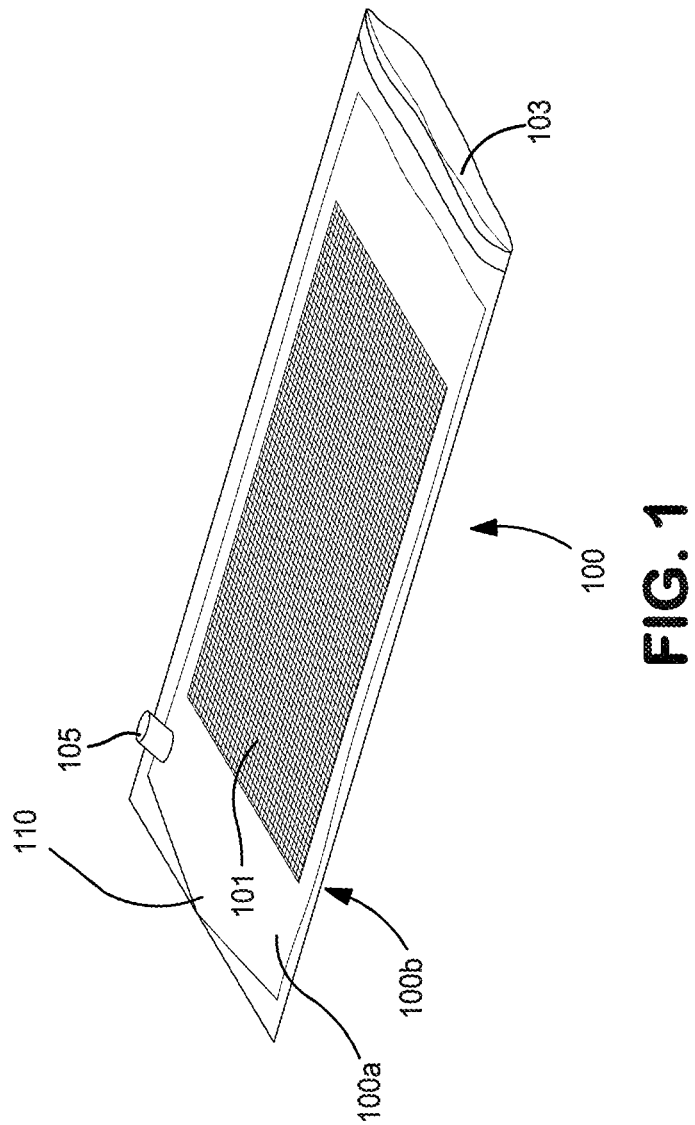
FIG. 1 is a perspective view of one illustrative embodiment of a sealed inner package for a lyophilized implant in accordance with the principles of a first embodiment of the invention.

FIG. 1 is a perspective view of a packaging method and apparatus for lyophilized implants in accordance with the principles of the present invention. The apparatus comprises a pouch 100 within which the lyophilized implant 101, such as a biologic tissue material or mesh material, is contained. The pouch is shown as transparent in the drawing so that the implant 101 can be seen in the drawing for sake of clarity. However, this is not necessary and, in fact, it may be undesirable to allow the implant to be exposed to light.

In any event, the pouch 100 may be formed of a flexible, but substantially non-stretchable material, such as Mylar™ with Tyvek™. The pouch preferable bears gussets 103 so that it can be folded into a substantially flat configuration, but, upon introduction of a pressurized liquid into the sealed pouch, the pouch can be expanded to a predetermined size, and particularly, a predetermined internal volume.

A rehydration port 105 is provided for permitting rehydration liquid to be introduced to the internal volume of the pouch preferably without exposing the implant within the inner pouch. In one preferred embodiment, the port 105 is a needleless port such as is commonly used with IV (intravenous) bags. Such ports comprise a resilient self-sealing material, such as a thermoplastic elastomer. The tip of a syringe (with or without a needle) may be forced through the port 105 and into the internal volume of the container with the port material sealing around the tip of the syringe. When the syringe tip is removed, the port material seals around the hole previously formed by the tip of the syringe to return the port back to a sealed condition.

In other embodiments, the port may be as simple as a screw cap, press cap, or other resealable port, including a resealable plastic zipper type closure system (such as found on Ziploc™ plastic food storage bags). In yet other embodiments, the port may be in the form of a Luer taper connector, which is a basic friction fit commonly used in many industries, including pharmaceuticals and health care. The Luer taper connector may feature a locking ring for a more secure connection. See, for instance, Luer-Lock; ANSI standard HIMA MD70.1, ANSI/AAMI Taper Luered Fitting Standard: and ISO 594-1 standards, such as ISO 594-1:1986.

The pouch itself may be comprised of two pieces 100a, 100b of the pouch material edge-sealed to each other. A first piece 100a may be in the form of a tray bearing gussets 103 so that it can be folded substantially flat. The second piece 100b may be a flat sheet. The two pieces are attached to each other at their respective edges 109a, 109b. The sealing may be achieved via an adhesive bead 115 (see FIG. 4) or a heat activation seal around the edges of the pieces. This seal should allow the two pieces 100a, 100b to be peeled away from each other using hand strength so as to allow the medical staff to open the pouch to remove the implant 101 from the pouch after it is rehydrated, as discussed below. A tab, such as chevron shaped tab 110 may be provided on one or both portions 100a, 100b of the pouch to provide a place to grip the pouch to pull the one portion, e.g., 100a apart at the seal 115 from the other portion, e.g., 100b to open the pouch and expose the implant for removal from the pouch 100.

In other embodiments, this second seal for opening the pouch for removal of the implant therefrom also may comprise a plastic zipper opening mechanism (like a Ziploc™ bag) or a weakened tearable strip (like a restaurant ketchup packet with serrated v-edges), or a perforated strip edge.

FIG. 5 illustrated yet another embodiment for applications in which it is desirable or at least optional to add another substance to the prosthesis or rehydration liquid during rehydration. The additional substance may, for instance, be an antibiotic drug, a medication, or a growth hormone. A vial or other container may contain the proper amount of such substance relative to the amount of rehydration liquid that can fit within the inner pouch when fully expanded to provide the desired concentration.

Referring to exemplary FIG. 5, the packaged product may be delivered with a vial 121 of the additional substance included in the overall packaging, such as enclosed within the outer pouch 200, and possibly attached to the outside of the inner pouch 100. The vial 121 can be opened, such as by breaking or tearing the vial or cutting the vial with a scissor or other cutting implement. Of course, one can mix the contents of the vial with the proper amount of rehydration liquid outside of the inner pouch 100, e.g., in a beaker, bowl, or other container, and then introduce the rehydration liquid containing the additive into the inner pouch 100 as previously described. However, in one preferred embodiment, the contents of the vial are poured into the inner pouch through the rehydration port 105 immediately before the rehydration liquid is introduced into the inner pouch (or possibly after some of the rehydration liquid has been introduced into the inner pouch 100, but before the pouch is fully expanded).

The contents of the vial may be in solid form (e.g., a powder) or liquid form.

In yet another embodiment best suited for vials with liquid contents, the contents of the vial may be withdrawn from the vial and introduced into the inner pouch by puncturing the vial with the needle of a syringe, withdrawing the contents with the syringe, and then injecting the contents into the inner pouch with the same syringe.

In another embodiment, the vial 121 may be attached to the outside of the inner pouch 100 via a breechable junction 123, such as a one-way valve (flow direction into the inner pouch) that has some minimum required pressure differential to open. In this manner, the doctor, nurse, or other personnel could simply squeeze the vial 121 just prior to, during, or after introduction of the rehydration fluid into the pouch to release the contents of the vial into the pouch.

In yet other embodiments, the junction 123 between the vial and the pouch may be any breakable barrier (e.g., puncturable) so that the inside of the vial 121 and the inside of the pouch 100 come into fluid communication with each other upon breakage of the junction 123. Such an embodiment may be desirable if the rehydration port 105 is in the form of a needleless port or other type of port through which it would be difficult or impossible to pour the contents of the vial into the pouch 100. Such a concern may be particularly acute if the contents of the vial are in powder or other solid form such that it cannot be injected through a needleless port. This may be accomplished, for instance, by sealing a part of the vial 121, e.g., the first longitudinal end 121a, to the surface of the inner pouch around the junction 123 and providing a sharp point 125 within the vial 121 adjacent the junction 123 that is sealed to the inner pouch 100, which point 125 can be used to puncture the inner pouch when desired. For instance, the first longitudinal end 121a of the vial 121 may be sealed to the pouch at junction 123 as described above while the second longitudinal end 121b (or any other part of the vial) is loosely adhered to the pouch 100 so that the second end 121b of the vial can be torn away from the pouch 100. When it is time to introduce the contents of the vial 121 into the pouch 100, the back end 121b of the vial 121 is tilted up relative to the pouch while the first end 121a is still attached to the pouch causing the sharp point 125 to puncture the pouch 100 at the junction within the area where the vial is sealed to the pouch. The seal between the pouch 100 and the vial 121 is broken so that the contents of the two become commingled, but the system is still sealed against the external environment. The vial may be squeezed if necessary to help force its contents into the inner pouch to better intermix its contents with the rehydration liquid in the inner pouch 100.

In use, the sterile pouch is delivered aseptically to the sterile operative field in a flattened condition, i.e., with the gussets 103 in a folded condition.

Figure 2:
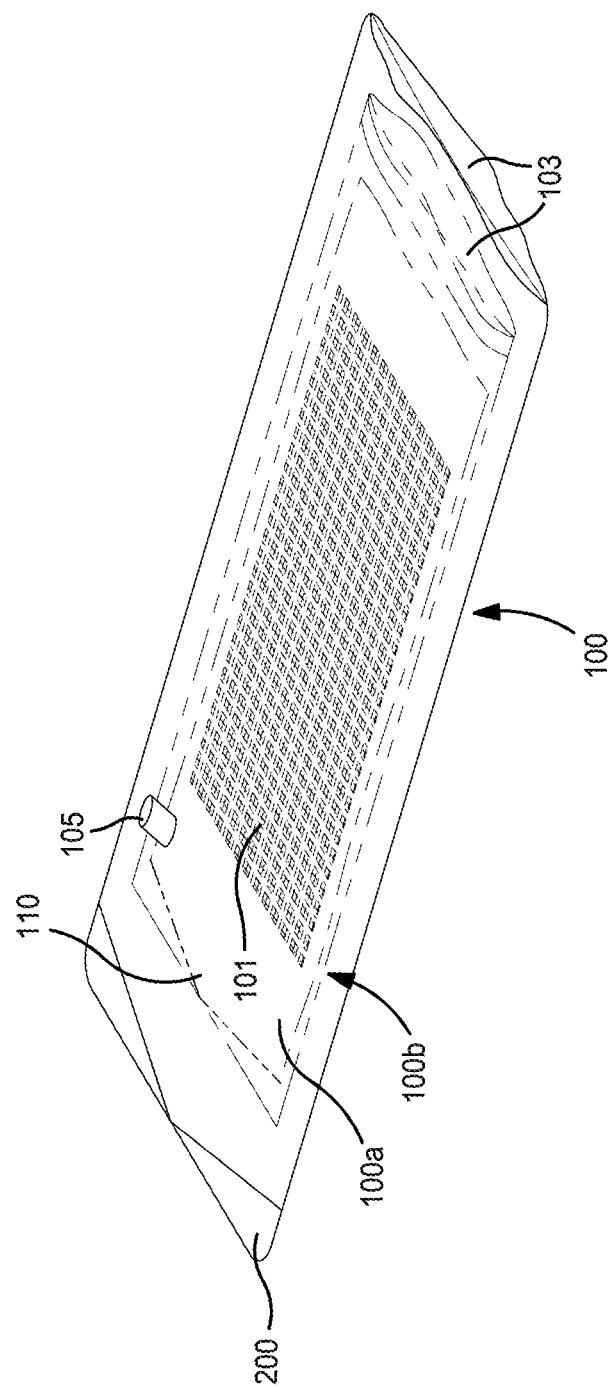
FIG. 2 is a partial see-through view of the inner package of FIG. 1 further packaged within an outer package in accordance with the principles of the invention.

In order to maintain the sterility of the pouch 100 when it is introduced into the sterile operative field, it may be packaged within a second, outer package at the manufacturing facility. The inner pouch (containing the also sterile implant) is sealed within the outer package at the manufacturing facility, and the inner and outer packages are sterilized by an acceptable method of sterilization. This is shown in FIG. 2, in which the inner pouch is packaged within an outer pouch 200. The outer pouch 200 may be any reasonable packaging apparatus for maintaining the inside of the sealed outer package in a sterile condition until the outer packaging is opened within the operating room for delivery to the sterile operative field. The outer packaging 200 may be substantially similar to the inner pouch 100 in terms of material, manner of sealing, and construction, but should be bigger than the inner pouch so that the inner pouch 100 can be entirely contained within the outer packaging 200.

The outer packaging is opened aseptically in the operative environment and the inner pouch 100 is delivered aseptically to the sterile surgical field.

Figure 3:
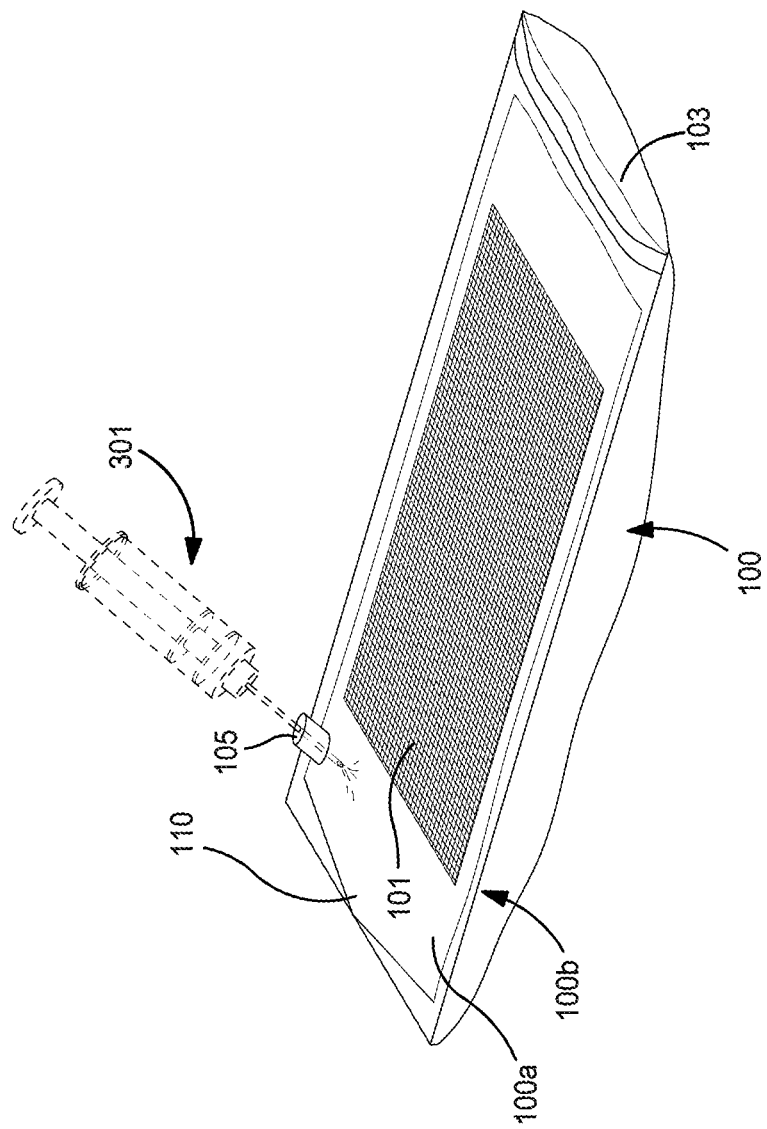
FIG. 3 is a perspective view of the inner package of FIG. 1 in its expanded configuration after the rehydration liquid has been introduced into its internal volume in accordance with the principles of the invention.

With reference to FIG. 3, at the appropriate time, the rehydration liquid is introduced into the internal volume of the pouch 100 through the rehydration port. For instance, in the needleless port embodiment illustrated in FIG. 3, the tip of a syringe 301 filled with the rehydration liquid 303 is inserted through the self sealing port 105 and the liquid 303 is injected into the internal space of the pouch. The rehydration liquid commonly comprises sterile saline. However, it may also contain or may have added to it growth factors, antibiotics, anti-coagulants or other medications or substances. Because the pouch is gusseted or otherwise expandable, the rehydration liquid will flow into the pouch and cause the pouch to expand, as shown (e.g., the gussets will unfold).

The configuration of the pouch, such as the configuration of the gussets, will allow the pouch to expand only to a predetermined internal volume, that volume preferably designed to allow the exact amount of rehydration liquid needed to properly rehydrate the implant to enter the pouch. After the pouch has fully expanded, the syringe is removed and the port resealed in accordance with its design. In the exemplary needleless port embodiment described herein, the port will self seal as soon as the syringe tip is removed from it.

In connection with the any of the embodiments such as discussed in FIG. 5 (in which a vial of additive substance is to be added to the prosthesis and/or rehydration liquid), the additive substance may be added to the pouch at this point. That may be performed in any of the manners discussed herein above. Alternately, also as previously noted, the additive may be added to the rehydration fluid externally of the pouch and the mixture added to the pouch.

The implant is then allowed to rehydrate for the amount of time specified by the manufacturer. At the end of that time, if there is any excess liquid still in the pouch (which, often, there will not be any liquid because the exact proper amount of rehydration fluid needed to rehydrate the implant was initially introduced into the pouch in accordance with the principles of the invention), any excess rehydration liquid may be removed via the rehydration port. For instance, in this embodiment, a syringe tip may be passed through the port and the plunger withdrawn to draw any excess liquid out of the pouch. A needleless approach is further beneficial because it minimizes the possibility of accidentally puncturing the pouch during introduction of the rehydration liquid into the pouch.

As another example, in a screw cap embodiment, the screw cap may be removed and any excess rehydration liquid simply may be poured out of the pouch. Whatever the form of the rehydration port, the opening created in it for adding or removing the rehydration liquid should be as small as reasonably possible and certainly small enough so that the implant cannot reasonably pass through it.

Figure 4:
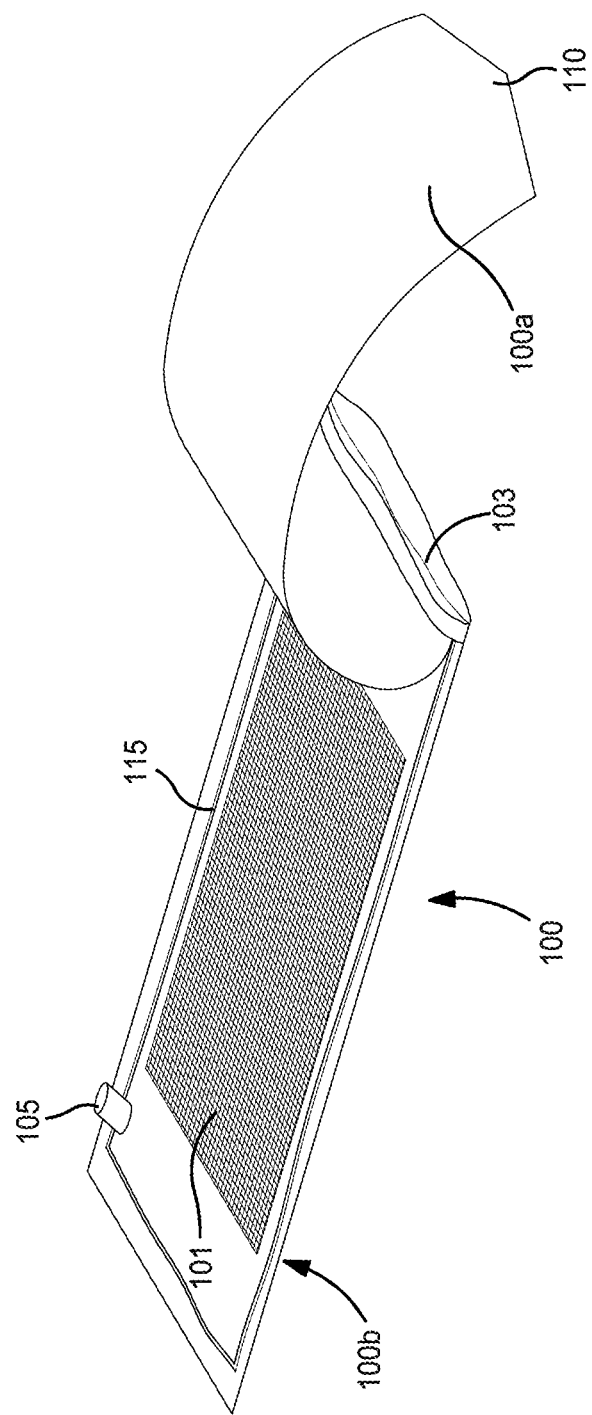
FIG. 4 is a perspective view of the inner package of FIG. 1 after it has been opened via the second opening in accordance with the principles of the invention to permit the implant to be removed therefrom.

Next, with reference to FIG. 4, the inner pouch is opened via the second opening mechanism. In this example, the tabs are grasped and pulled away from each other to tear the two pouch portions 100a, 100b apart from each other at the adhesive bead 115 or heat seal as previously described, thereby exposing the implant 101 for removal from the pouch for implantation.

Thereafter, the implant is removed and implanted in accordance with the particular surgical procedure.

The packaging and rehydration solution of the present invention maintains the implant in a substantially sealed sterile package until just prior to implantation. It also closely controls the amount of rehydration liquid that can be introduced to the implant. Specifically, it is virtually impossible to overhydrate because the pouch simply cannot accept more than a predetermined amount of rehydration liquid. Furthermore, it is difficult to underhydrate the implant because the pouch provides a simple tactile or visual cue as to when the pouch is fully filled. Essentially, one must introduce liquid until the pouch is fully expanded. In the needleless port embodiment, for instance, the person rehydrating the implant should keep injecting the rehydration liquid into the pouch until it becomes difficult to inject further liquid.

Furthermore, the packaging folds virtually flat before rehydration so that the product can be shipped and stored flat, thus saving transportation cost and shelf space during storage. Of course, the use of the packaging of the invention in connection with a substantially flat prosthesis is merely exemplary. The inventive packaging may be used to package any medical implement, including implants, prostheses, biologic materials, instruments, and devices, and is capable of being folded or other wise reduced in size and shape to substantially conform to the thing contained within it for minimal storage and shipping space. Yet further, the implant remains within a substantially sealed pouch during rehydration so that evaporation and contamination are avoided. Furthermore, because the pouch remains substantially sealed during the period of rehydration, the rehydration liquid cannot be spilled during this time. Furthermore, when the pouch is opened at the second opening for removing the hydrated implant, there should be no excess liquid within the pouch such that chances for spillage of rehydration liquid are even further diminished. Furthermore, there is no flotation issue because the implant remains within a sealed container during rehydration that contains nothing but the implant and rehydration liquid.

Having thus described a few particular embodiments of the invention, various alterations, modifications, and improvements will readily be obvious to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A method of storing and rehydrating a lyophilized medical implement, the method comprising:
   sealing the lyophilized medical implement within a sealed flexible container capable of being expanded away from the lyophilized medical implement to a maximum predetermined internal volume, the maximum predetermined internal volume corresponding to a certain volume of rehydration fluid for properly hydrating the lyophilized medical implement, the flexible container including a resealable port for receiving rehydration liquid therethrough into the flexible container;
   opening the resealable port and introducing rehydration liquid into the flexible container through the resealable port until the flexible container has expanded to the maximum, predetermined internal volume;
   resealing the resealable port;
   waiting for the lyophilized medical implement to rehydrate within the sealed resealable container;
   opening the sealed flexible container via a second opening through which the medical implement may be removed from the resealable container; and
   removing the medical implement from the flexible container.

2. The method of claim 1 further comprising:
   removing any excess rehydration liquid from the flexible container after the waiting and before opening the second opening of the flexible container.

3. The method of claim 1 wherein the opening the resealable port and the introducing of rehydration liquid comprise filling the flexible container with rehydration liquid until the flexible container has expanded to the maximum predetermined volume.

4. The method of claim 3 wherein the resealable port comprises a needleless port and the opening the resealable port and the introducing of rehydration fluid comprises puncturing the resealable port with a syringe containing the rehydration fluid and injecting the rehydration fluid from the syringe into the flexible container.

5. The method of claim 1 wherein the flexible container comprises first and second container components sealed to each other via a separable seal and the opening of the second opening comprises separating the first and second flexible container components from each other at the separable seal.

6. The method of claim 1 further comprising:
   sealing the flexible container within an outer container;
   sterilizing the flexible container; and
   opening the outer container to expose the flexible container.

7. The method of claim 6 wherein the outer container comprises first and second outer container components sealed to each other via a second separable seal and wherein the opening of the outer container comprises separating the first and second outer container components from each other at the second separable seal.

8. The method of claim 1 further comprising introducing an additive substance into the sealed flexible container independently of the introduction of the rehydration fluid into the sealed flexible container.

* * * * *